(12) United States Patent
Austin et al.

(10) Patent No.: US 6,935,459 B2
(45) Date of Patent: Aug. 30, 2005

(54) RESONATING DEVICE FOR A PNEUMATIC SURGICAL INSTRUMENT

(75) Inventors: Tim Austin, Portage, MI (US); Steve Reasoner, Kalamazoo, MI (US)

(73) Assignee: Stryker Instruments, Kalamazoo, MI (US)

( * ) Notice: Subject to any disclaimer, the term of this patent is extended or adjusted under 35 U.S.C. 154(b) by 287 days.

(21) Appl. No.: 10/374,362

(22) Filed: Feb. 25, 2003

(65) Prior Publication Data

US 2004/0163884 A1 Aug. 26, 2004

(51) Int. Cl.⁷ .................................................. B21J 1/00
(52) U.S. Cl. ..................................................... 181/230
(58) Field of Search ................................. 181/230, 210, 181/211, 212–217, 220, 226, 227–229, 232

(56) References Cited

U.S. PATENT DOCUMENTS

| | | |
|---|---|---|
| 3,946,735 A | 3/1976 | DeWall |
| 4,091,892 A | 5/1978 | Hehmann et al. |
| 4,258,824 A | 3/1981 | Kurtz et al. |
| 4,683,884 A * | 8/1987 | Hatfield et al. ............... 606/49 |
| 4,929,244 A | 5/1990 | Swisher |
| 5,354,268 A | 10/1994 | Peterson et al. |
| 5,417,655 A | 5/1995 | Divilio et al. |
| 5,466,229 A | 11/1995 | Elson et al. |
| 5,607,411 A | 3/1997 | Heironimus et al. |
| 5,996,733 A | 12/1999 | DeTuncq et al. |
| 6,009,705 A | 1/2000 | Arnott et al. |
| 6,048,386 A | 4/2000 | Gillingham et al. |
| 6,201,872 B1 | 3/2001 | Hersh et al. |
| 2004/0225293 A1 * | 11/2004 | Tidwell et al. |

OTHER PUBLICATIONS

Joe Wolfe, Helmholtz Resonance, www.phys.unsw.edu.au/~jw/Helmholtz.htm.

* cited by examiner

Primary Examiner—Kimberly Lockett
(74) Attorney, Agent, or Firm—David M. Laprairie; Howard & Howard

(57) ABSTRACT

A resonating device for attenuating sound waves that are generated by a pneumatic surgical instrument is disclosed. The resonating device includes a manifold having a duct for accommodating a flow of fluid from the instrument. A plurality of canisters extend from the manifold for attenuating sound waves produced by the instrument. A neck extends into each canister and is in fluid communication with the duct and the canister. The canisters are mounted to and extend from the manifold in series. The canisters attenuate the sound waves in order from the highest frequency to the lowest frequency, thereby efficiently attenuating the sound waves.

66 Claims, 10 Drawing Sheets

RESONATING DEVICE FOR A PNEUMATIC SURGICAL INSTRUMENT

BACKGROUND OF THE INVENTION

1) Field of the Invention

The subject invention relates to a resonating device for attenuating sound waves that are generated by a pneumatic surgical instrument during surgery.

2) Description of the Related Art

Various resonating devices for attenuating sound waves are well known in the art. Commonly referred to as Helmholtz resonators, resonating devices are characterized by a container of fluid, usually air, with an open hole. The fluid can generally be any gas. The resonating devices often include a neck extending from the container. The neck defines the open hole at an end of the neck that is distal from the container. The most common example of a resonating device is an empty pop bottle. The resonating effect is illustrated as a person blows air across the open hole of the bottle to produce a sound.

Resonating devices operate on the well known principle of the Helmholtz equation, as set forth below:

$$F = \frac{C}{2\Pi}\sqrt{\frac{A}{VL}}$$

where F is a frequency produced by the resonator and is a constant with respect to the dimensions of the resonating device, C is a velocity of sound at a given temperature, A is a cross-sectional area of the open hole, V is a volume of the container, and L is a length of the hole. The equation is most easily illustrated by blowing across the top of a pop bottle, i.e. the container. By adding liquid into the bottle, which decreases the volume of the bottle, a change in sound tone can be observed resulting from the decrease in volume of the bottle.

Although resonating devices are used to produce sound, as in the aforementioned example, resonating devices are also used to eliminate sound. Resonating devices are often connected to a flow of fluid. The flow of fluid has loud sound waves traveling through it. As the flow of fluid travels through the resonating device, the fluid causes the resonating device to produce sound waves that attenuate sound waves at the same frequency traveling through the flow of fluid.

Resonating devices are widely used in automobile exhaust applications for attenuating sound waves generated by an engine. The resonating devices are generally connected to an exhaust line. Exhaust gas from the engine passes across the open hole of the resonating devices and produces sound waves. The sound waves produced by the resonating devices attenuate the sound waves produced by the engine.

Prior art resonating devices generally include a housing having an inlet, outlet, and a duct connecting the inlet to the outlet. One or more containers are generally contained within the housing and connect to the duct. The containers generally define a cavity with a neck connecting the cavity to the duct. Although multiple containers of different sizes are often used to attenuate sound waves at multiple frequencies, the prior art merely positions the containers randomly, according to space constraints, but does not suggest ordering the resonators to increase sound attenuation efficiency.

The prior art resonating devices fail to suggest extending and suspending the full neck into the volume of the container. The prior art also fails to suggest separating the neck from the container of the resonator. The prior art resonating devices require special manufacturing to achieve the dimensions required to attenuate sound waves at a specific frequency and cannot be constructed with pre-existing parts.

Furthermore, prior art resonating devices have not been applied to surgical instrument arts. Operating rooms in which surgical instruments are employed are generally small and congested. The operating rooms, when in use, are filled with surgical instruments needed for surgery. Many people often fill the operating rooms as well, including doctors and nurses, not to mention the patient. Therefore, a premium is placed upon surgical instruments that are minimal in size without compromising performance. In addition, resonating devices are required to eliminate the sound waves produced by the surgical instruments, which inhibit communication and concentration within the operating room. As a result of size constraints, the resonating devices of the prior art are too large and bulky and are therefore not practical for application to surgical arts.

Thus, there remains an opportunity for a resonating device for use in the surgical arts which is compact yet can be easily manufactured with pre-existing parts to attenuate sound waves with greater efficiency than existing resonating devices.

BRIEF SUMMARY OF THE INVENTION AND ADVANTAGES

The invention provides a resonating system for attenuating sound waves that are generated by a pneumatic surgical instrument during surgery. The resonating system includes the pneumatic surgical instrument and a resonating device. The resonating device includes a manifold, at least one canister, and a neck. The manifold is in fluid communication with the surgical instrument and has an inlet and an outlet. The manifold defines a duct extending between the inlet and the outlet for accommodating a flow of fluid from the surgical instrument. Fluid refers to air or any gas in general that can be employed to generate vacuum pressure for the pneumatic surgical instrument. Fluid does not refer to liquid that is collected by the surgical instrument, during surgery. The canister extends from the manifold and defines a volume for attenuating the sound waves generated by the surgical instrument. The system and the device are characterized by the neck, which is in fluid communication with the duct, extending into the canister to minimize the size of the resonating device.

The subject invention also provides a resonating device for attenuating sound waves at different harmonic frequencies. The canister and the second canister extend from the manifold in series. The canister defines a volume for attenuating the sound waves that are generated by the surgical instrument at a first harmonic frequency. The second canister defines a volume for attenuating the sound waves that are generated by the surgical instrument at a second harmonic frequency. The first harmonic frequency is a lowest harmonic frequency and the second harmonic frequency is greater than the first harmonic frequency. The resonating device is characterized by the second canister extending from the manifold closer to the inlet than the canister. As such, the sound waves that are generated at the second harmonic frequency are attenuated by the second canister before the sound waves that are generated at the first harmonic frequency are attenuated by the canister upon flow of the fluid into said manifold through the inlet.

Accordingly, the resonating device of the subject invention is sufficiently compact to fit within a limited amount of space available in a resonating system in combination with a pneumatic surgical instrument without requiring special manufacturing techniques to produce. Furthermore, the order of the canisters allows the resonating device to attenuate sound waves more efficiently than resonating devices of the prior art.

BRIEF DESCRIPTION OF THE SEVERAL VIEWS OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
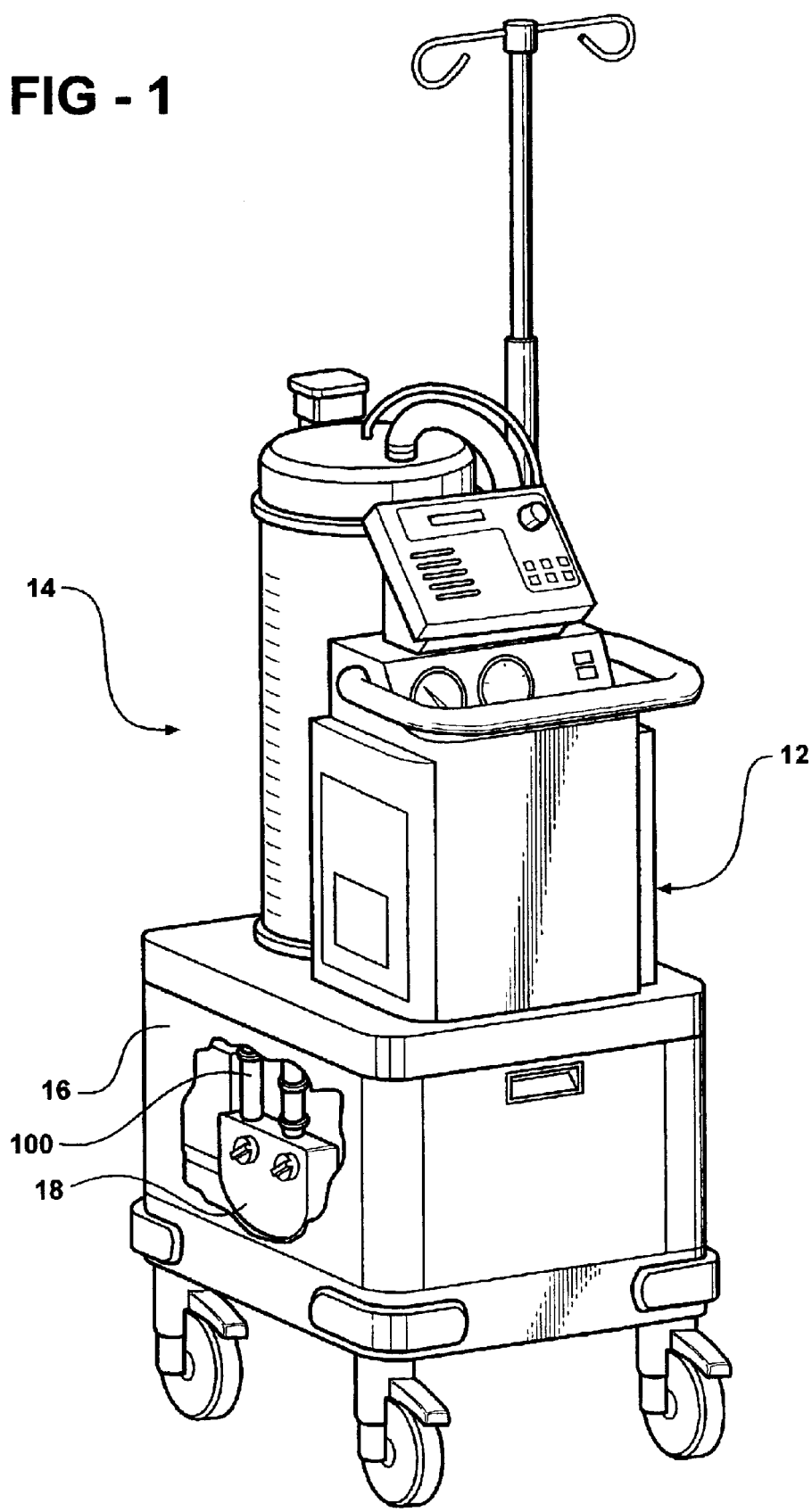
FIG. 1 is a perspective view of a resonating system including a pneumatic surgical instrument and a partially cutaway view of a cabinet of the resonating system.

Referring to the Figures, wherein like numerals indicate like or corresponding parts throughout the several views, a resonating device is shown generally at 10. The resonating device 10 attenuates sound waves that are generated by a pneumatic surgical instrument 12, shown in FIG. 1, during surgery.

Preferably, the pneumatic surgical instrument 12 is a vacuum suction instrument used for removing waste during surgery. Typical wastes removed during surgery include liquids such as blood and saline, small solids such as bone fragments, and semi-solid matter such as fat and other body tissue. To accomplish, the pneumatic surgical instrument 12 can include a surgical tool such as a suction wand 11. The wastes are removed with the suction wand 11 and deposited in a waste collection bin 13.

The resonating device 10 and the pneumatic surgical instrument 12 are components of a resonating system 14.

The resonating system 14 is designed for use in surgical operating rooms. Space is limited in a surgical operating room and the resonating system 14 is compact yet powerful.

Figure 2:
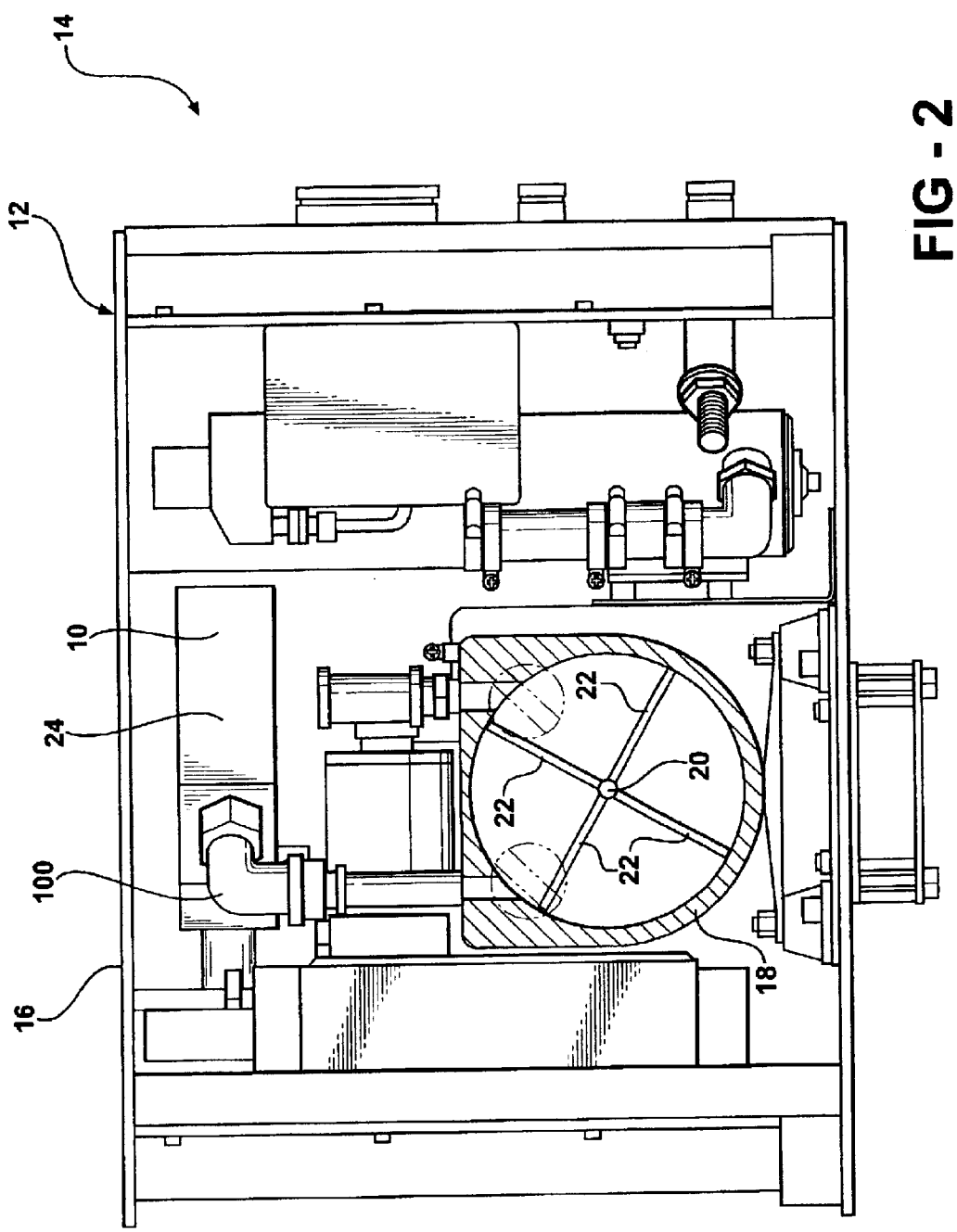
FIG. 2 is a partially cross-sectional view of the cabinet illustrating a pump and resonating device within the cabinet.

The resonating system 14 includes a cabinet 16. The cabinet 16 houses parts of the pneumatic surgical instrument 12 and the resonating device 10. Referring to FIGS. 1 and 2, the pneumatic surgical instrument 12 also includes a pump 18 housed within the cabinet 16. The pump 18 supplies a flow of fluid to the pneumatic surgical instrument 12. Preferably, the fluid is air, but can also be any other gas. Fluid refers to air or any gas in general that is employed to generate vacuum pressure for the pneumatic surgical instrument 12. Fluid, as used herein, does not refer to liquid or any other material that is collected by the pneumatic surgical instrument 12 during surgery. Generally, the pump 18 is of the rotary vane type, but can be any type of vacuum pump capable of supplying the flow of fluid to the pneumatic surgical instrument 12. Ideally, the pump 18 is as powerful as possible. Pump power is generally proportional to pump size. Thus, the size of the pump 18 is as large as can fit in the cabinet 16. Preferably, the pump 18 is a Gast 1023 Series 12 CFM pump available from Gast Manufacturing, Incorporated, a unit of IDEX Corporation of Northbrook, Ill. The pump 18 is capable of generating vacuum pressures of 0 to 26 in Hg, but can be larger or smaller depending on the size of the cabinet 16. Because the size of the pump is maximized, the resonating device 10 is sufficiently compact to fit within the cabinet 16 along with the pump 18.

Shown in FIG. 2, the pump 18 includes a shaft 20 that rotates a plurality of vanes 22 for flowing the fluid from the pneumatic surgical instrument 12 to the resonating device 10. The rotation of the plurality of vanes 22 produces loud sound waves at a first harmonic frequency $F_1$, a second harmonic frequency $F_2$, a third harmonic frequency $F_3$, etc. The sound waves at the first harmonic frequency $F_1$, second harmonic frequency $F_2$, and third harmonic frequency $F_3$ are louder than other sound waves produced by the pneumatic surgical instrument 12. The sound waves emanate from the pump 18 and travel through the fluid. The ability to effectively eliminate the sound waves is hindered by the small space available to do so. The resonating device 10 of the subject invention is sufficiently compact to fit within the cabinet 16 and more effectively eliminates the sound waves traveling through the fluid than other types of devices currently in use.

Figure 3:
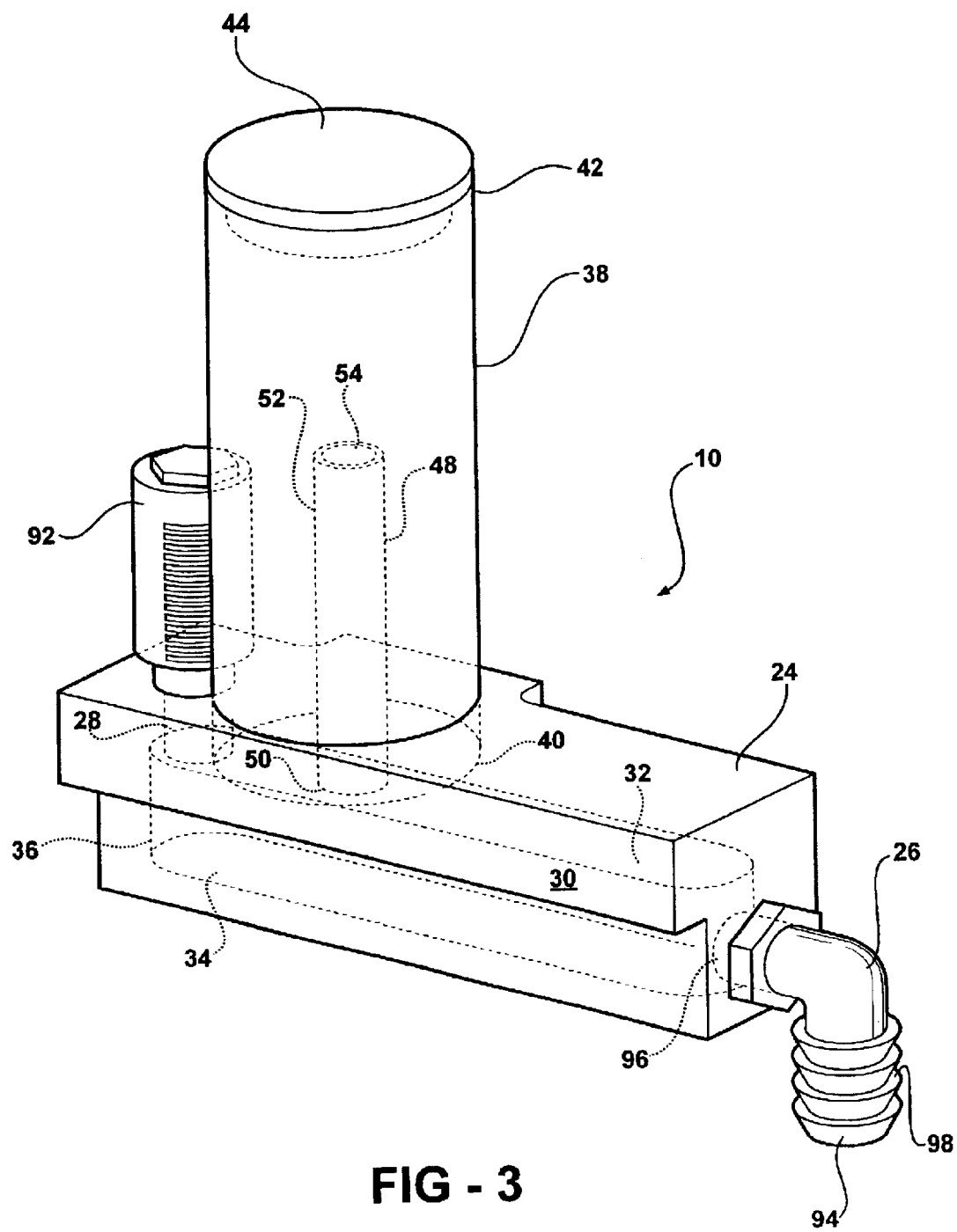
FIG. 3 is a perspective view of the resonating device including a neck and a canister with the neck extending into the canister.

As shown in FIG. 3, the resonating device 10 includes a manifold 24, which includes an inlet 26 and an outlet 28. The manifold 24 defines a duct 30 extending between the inlet 26 and the outlet 28 for accommodating the flow of fluid from the pneumatic surgical instrument 12. The manifold 24 further defines the duct 30 with a top surface 32, a bottom surface 34, and a peripheral wall 36 connecting the surfaces 32, 34.

Figure 8:
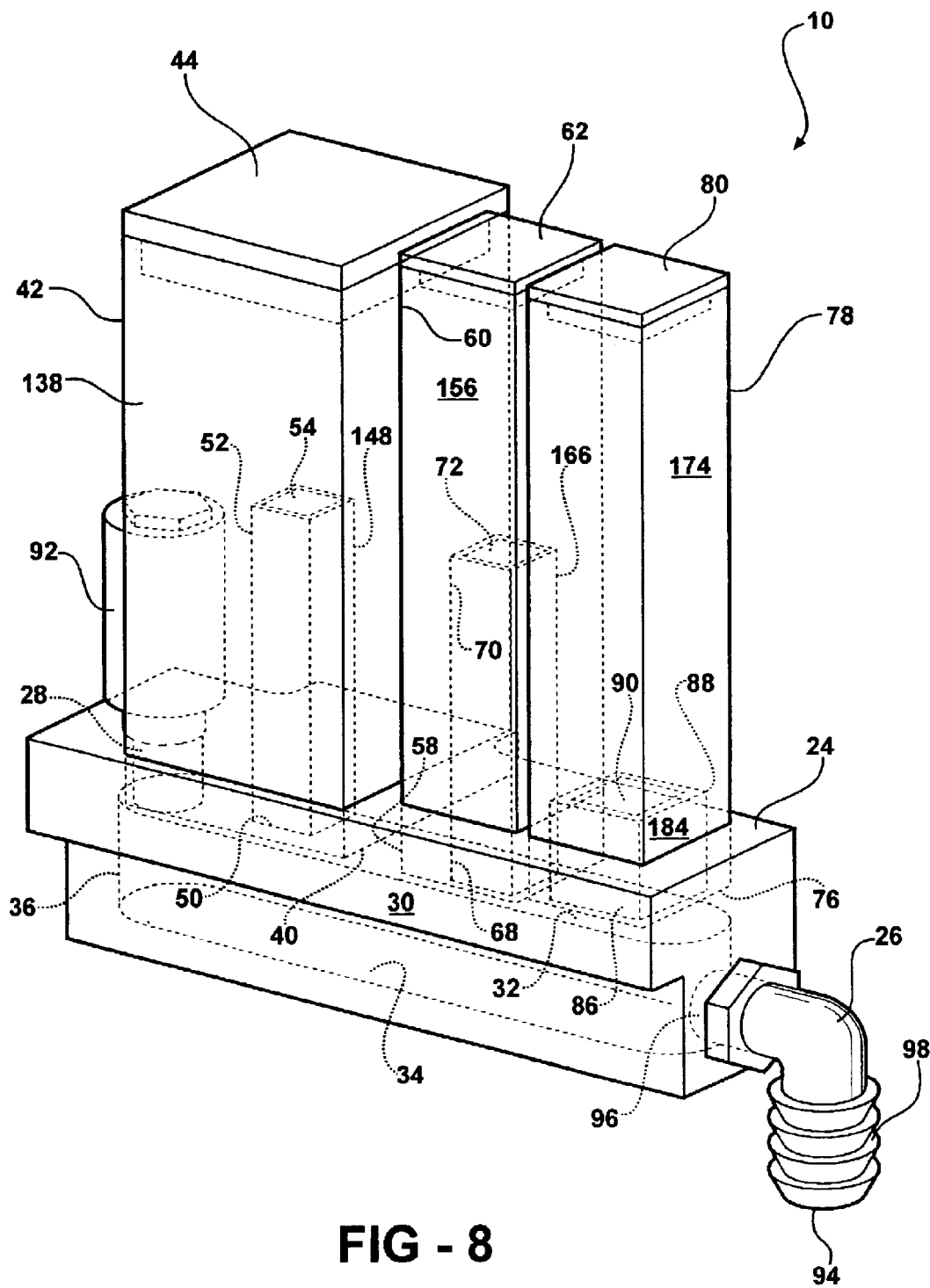
FIG. 8 is a perspective view of another embodiment of the resonating device including box-shaped canisters, box-shaped necks, and box-shaped caps.

As the fluid from the pneumatic surgical instrument 12 passes through the duct 30, the sound waves traveling in the fluid are attenuated by at least one canister 38 that extends from the manifold 24. The canister 38 defines a volume $V_1$ for attenuating the sound waves generated by the pneumatic surgical instrument 12 at the first harmonic frequency $F_1$. Preferably, the canister 38 is cylindrical in shape. However, the canister 38 is not limited to a cylinder and can be of any number of shapes, such as the box-shaped canister 138 of FIG. 8, without deviating from the subject invention. A first end 40 of the canister 38 is connected to and extends into the manifold 24. A second end 42 of the canister 38 is sealed.

Figure 7:
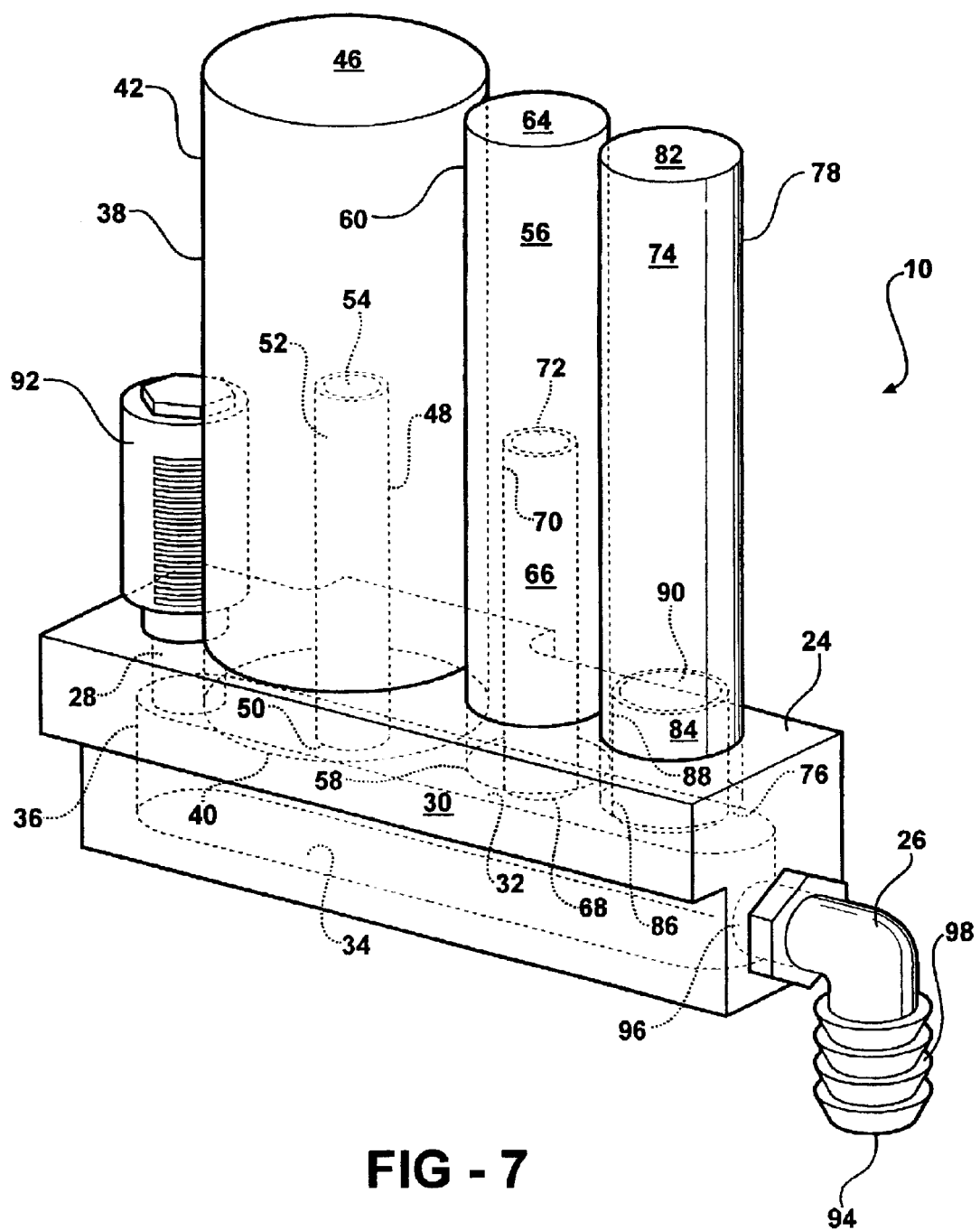
FIG. 7 is a perspective view of the resonating device of FIG. 5 including the canister, second canister, and third canister with end caps integrally molded onto the canisters.

The canister 38, shown in FIG. 7, is molded such that, by itself, it completely defines the volume $V_1$. As such, the second end 42 of the canister 38 is sealed. However, with reference to the embodiment disclosed in FIG. 3, a cap 44 may be inserted into the second end 42 of the canister 38 and secured with adhesive to seal the second end 42 of the canister 38. The cap 44 partially extends into the canister 38 to decrease the volume $V_1$ and to increase contact surface area between the cap 44 and the canister 38 for the adhesive.

A neck 48 is in fluid communication with the duct 30. Furthermore, to minimize the size of the resonating device 10 such that the resonating device 10 is sufficiently compact and can fit into the cabinet 16 with the pump 18, the neck 48 extends into the canister 38. More specifically, the neck 48 includes a proximal end 50 adjacent to the manifold 24 and a distal end 52 opposite the proximal end 50 and defines a neck duct 54 extending between the ends 50, 52. The distal end 52 is suspended in the volume $V_1$ of the canister 38. That is, the neck 48 is not in contact with the canister 38. The neck 48 is mounted on the manifold 24 at the proximal end 50. The duct 30 is in fluid communication with the canister 38 through the neck duct 54. The distal end 52 of the neck 48 is suspended in the canister 38, as opposed to connecting the canister 38 to the distal end 52 of the neck 48, to maintain structural integrity of the resonating device 10 and to keep the resonating device 10 compact. Preferably, the neck 48 is cylindrical in shape. However, it is to be appreciated that the neck 48 can be of any number of shapes, such as the box-shaped neck 148 of FIG. 7, without deviating from the subject invention.

The first harmonic frequency $F_1$ is the frequency at which the sound waves are the loudest. Thus, a significant noise reduction is achieved by attenuating the sound waves at the first harmonic frequency $F_1$. The first harmonic frequency $F_1$ is defined by the following equation:

$$F_1 = R*N$$

where $F_1$ is the first harmonic frequency, R is a number of rotations of the shaft per second, and N is a number of vanes 22. Preferably, R is 25 or greater and N is 4 or greater. More preferably, R is 29 and N is 4. The first harmonic frequency $F_1$ is also defined by the following equation:

$$F_1 = \frac{C}{2\Pi}\sqrt{\frac{A_1}{V_1 L_1}}$$

where $F_1$ is the first harmonic frequency and is a constant with respect to the resonating device 10, C is a velocity of sound at 17° C., $A_1$ is a cross-sectional area of the neck 48, $V_1$ is the volume of the canister 38, and $L_1$ is a length of the neck 48. Thus, by fixing the dimensions of the canister 38 and neck 48, the resonating device 10 is tuned to attenuate sound waves at the first harmonic frequency $F_1$. In the preferred embodiment, the first harmonic frequency $F_1$ is 100 Hertz or greater. More preferably, the first harmonic frequency $F_1$ is 116 Hertz. The canister 38 and neck 48 can be tuned to attenuate sound waves at various frequencies.

Figure 4:
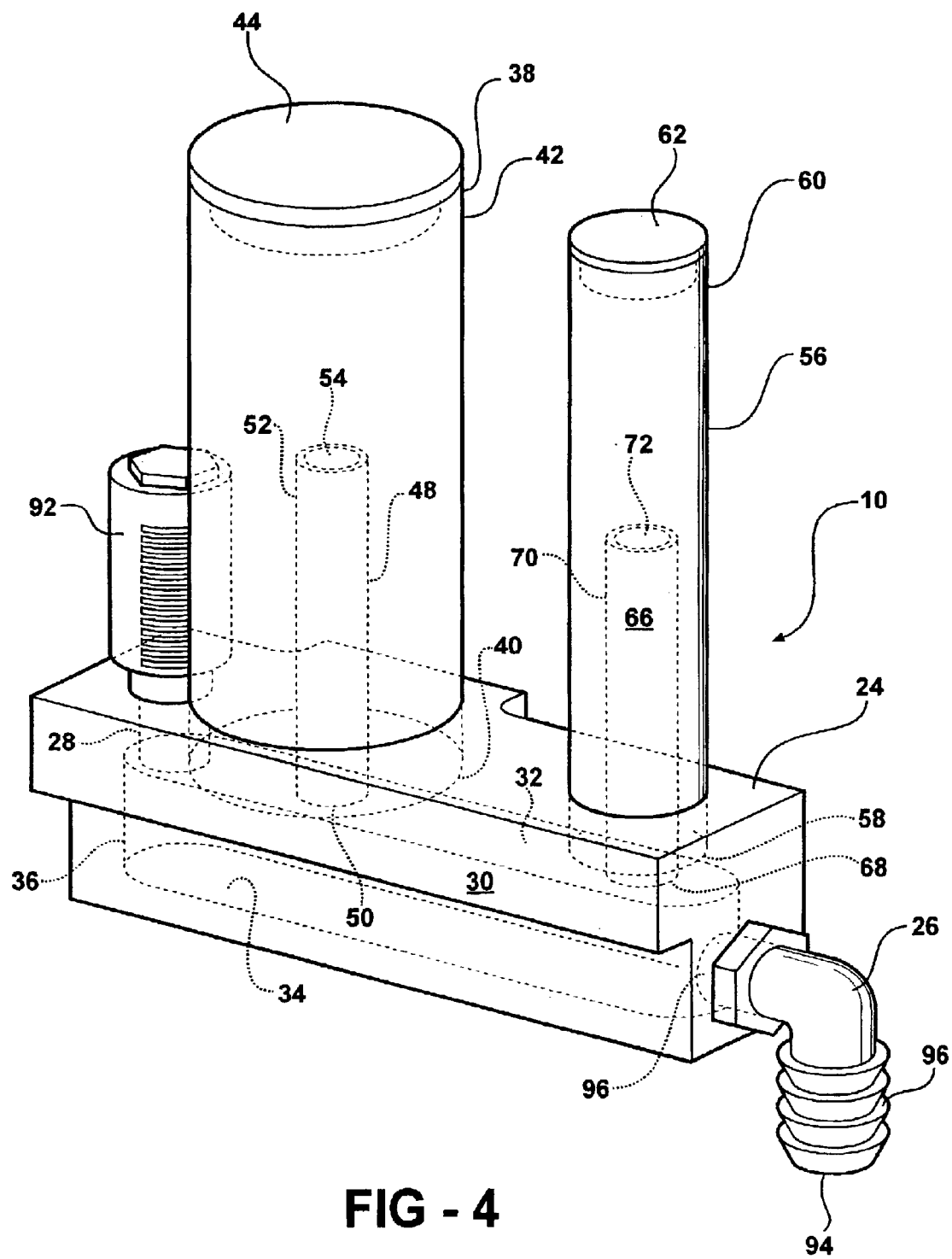
FIG. 4 is a perspective view of the resonating device including the canister and a second canister with necks extending into both of the canisters.

Preferably, as shown in FIG. 4, a plurality of canisters 55 extend from the manifold 24. More specifically, the resonating device 10 disclosed in FIG. 4 includes the canister 38 and a second canister 56. The second canister 56 attenuates the sound waves at the second harmonic frequency $F_2$. Preferably, the second canister 56 extends from the manifold 24 independent of the canister 38. Preferably, the canisters 38, 56 are on one side of the manifold 24 and are of relatively equal length to keep the resonating device 10 compact. However, the canisters 38, 56 can be on different sides of the manifold 24 and of different lengths. As the fluid passes from the pneumatic surgical instrument 12 through the duct 30, the sound waves traveling in the fluid are attenuated by the canisters 38, 56 that extend from the manifold 24. The second canister 56 defines a volume $V_2$ for attenuating the sound waves generated by the pneumatic surgical instrument 12 at the second harmonic frequency $F_2$. Preferably, the second canister 56 is cylindrical in shape. However, the second canister 56 is not limited to a cylinder and can be of any number of shapes, such as the second box-shaped canister 156 of FIG. 8, without deviating from the subject invention. A first end 58 of the second canister 56 is connected to and extends into the manifold 24. A second end 60 of the second canister 56 is sealed.

The second canister 56, as shown in FIG. 7, is molded such that, by itself, it completely defines the volume $V_2$. As such, the second end 60 of the second canister 56 is sealed. However, with reference to the embodiment disclosed in FIG. 4, a second cap 62 is inserted into the second end 60 of the second canister 56 and secured with adhesive to seal the second end 60 of the second canister 56. The second cap 62 partially extends into the second canister 56 to decrease the volume $V_2$ of the second canister and to increase contact surface area between the second cap 62 and the second canister 56 for the adhesive.

A second neck 66 is in fluid communication with the duct 30. Furthermore, to minimize the size of the resonating device 10 such that the resonating device 10 is sufficiently compact and can fit into the cabinet 16 with the pump 18, the second neck 66 extends into the second canister 56. More specifically, the second neck 66 includes a proximal end 68 adjacent to the manifold 24 and a distal end 70 opposite the proximal end 68 and defines a second neck duct 72 extending between the ends 68, 70. The distal end 70 of the second neck 66 is suspended in the volume $V_2$ of the second canister 38. That is, the second neck 66 is not in contact with the second canister 56. The second neck 66 is preferably of equal length and cross-sectional area as the neck 48, but can be of a different length and cross-sectional area than the neck 48. The second neck 66 is mounted on the manifold 24 at the proximal end 68 of the second neck 66. The duct 30 is in fluid communication with the second canister 56 through the second neck duct 72. The distal end 70 of the second neck 66 is suspended in the second canister 56, as opposed to connecting the second canister 56 to the distal end 70 of the second neck 66, to maintain structural integrity of the resonating device 10 and to keep the resonating device 10 compact. Preferably, the second neck 66 is cylindrical in shape. However, it is to be appreciated that the second neck 66 can be of any number of shapes, such as the second box-shaped neck 166 of FIG. 8, without deviating from the subject invention.

The second harmonic frequency $F_2$ is double the first harmonic frequency $F_1$ and is the frequency at which the sound waves are the next loudest to the first harmonic frequency $F_1$. Thus, a greater noise reduction is achieved by attenuating the sound waves at the first harmonic frequency $F_1$ and the second harmonic frequency $F_2$ than by merely attenuating the sound waves at the first harmonic frequency $F_1$. The second harmonic frequency $F_2$ is defined by the following equation:

$$F_2 = \frac{C}{2\Pi}\sqrt{\frac{A_2}{V_2 L_2}}$$

where $F_2$ is the second harmonic frequency and is a constant with respect to the resonating device 10, C is the velocity of sound at 17° C., $A_2$ is a cross-sectional area of the second neck 66, $V_2$ is the volume of the second canister 56, and $L_2$ is a length of the second neck 66. Preferably, the second harmonic frequency $F_2$ is 200 Hertz or greater. More preferably, the second harmonic frequency $F_2$ is 232 Hertz. The second canister 56 and second neck 66 can be tuned to attenuate sound waves at various frequencies.

Figure 5:
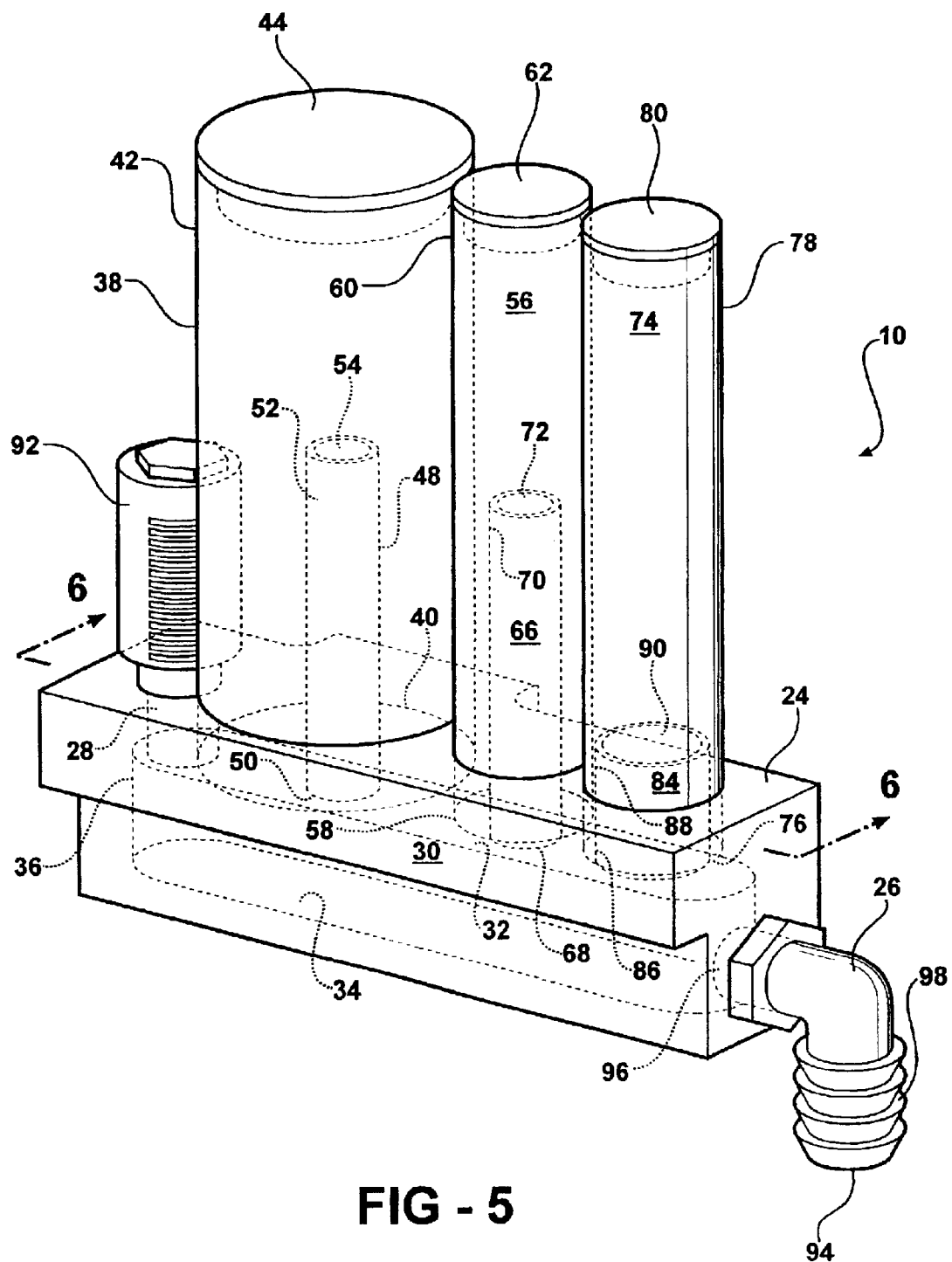
FIG. 5 is a perspective view of the resonating device including the canister, the second canister, and a third canister with necks extending into all of the canisters.
Figure 6:
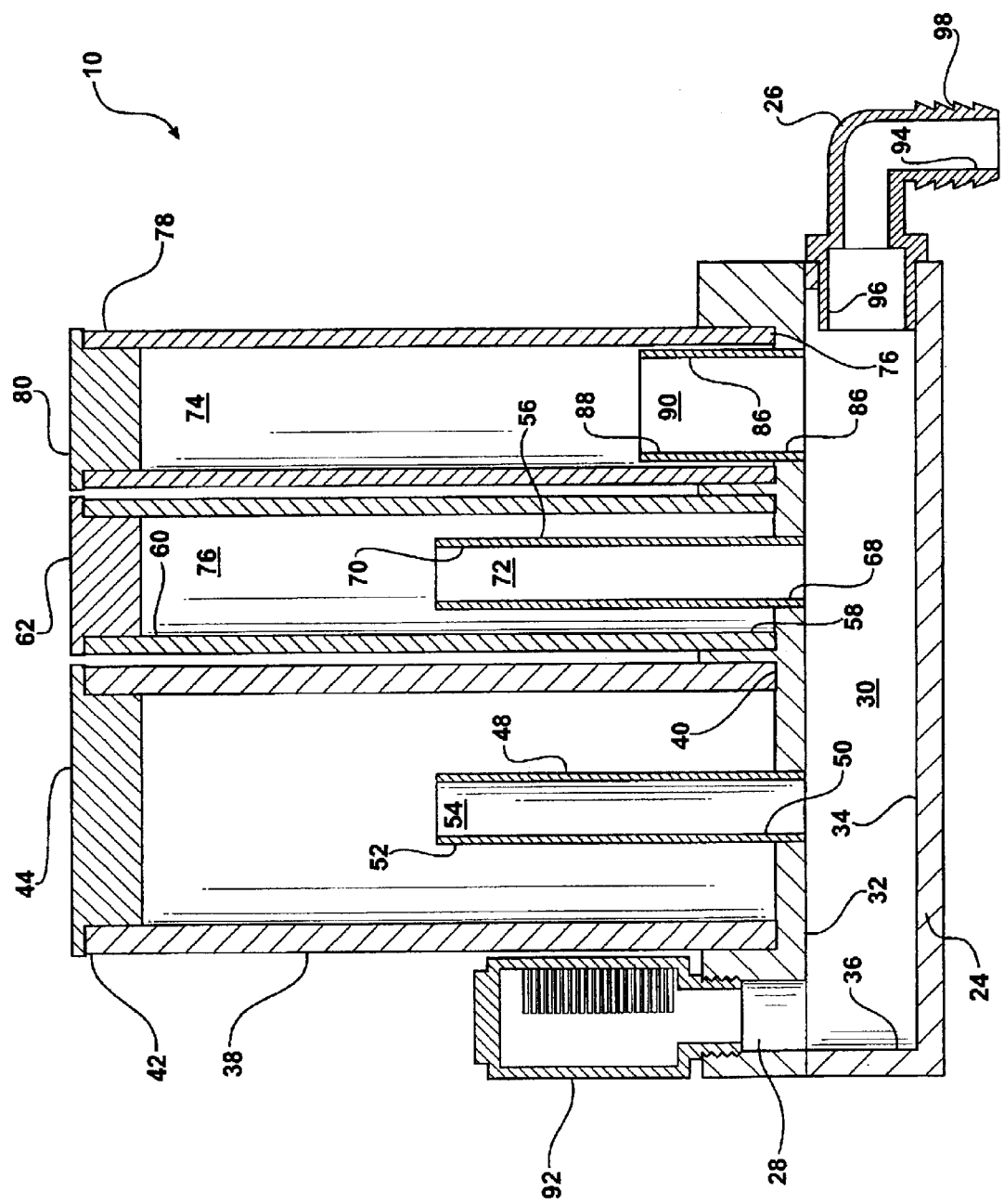
FIG. 6 is a partially cross-sectional side view of the resonating device of FIG. 5.

Most preferably, as shown in FIG. 5, the plurality of canisters 55 includes a third canister 74. More specifically, the resonating device disclosed in FIG. 5 includes the canister 38, the second canister 56, and the third canister 74. The third canister 74 attenuates the sound waves at the third harmonic frequency $F_3$. Preferably, the third canister 74 extends from the manifold 24 independent of the second canister 56 and the canister 38. Preferably, the canisters 38, 56, 74 are on one side of the manifold 24 and are of relatively equal length to keep the resonating device 10 compact. However, the canisters 38, 56, 74 can be on different sides of the manifold 24 and of different lengths. As the fluid passes from the pneumatic surgical instrument 12 through the duct 30, the sound waves traveling in the fluid are attenuated by the canisters 38, 56, 74 that extend from the manifold 24. The third canister 74 defines a volume $V_3$ for attenuating the sound waves generated by the pneumatic surgical instrument 12 at the third harmonic frequency $F_3$. Preferably, the third canister 74 is cylindrical in shape. However, the third canister 74 is not limited to a cylinder and can be of any number of shapes, such as the third box-shaped canister 174 of FIG. 8, without deviating from the subject invention. A first end 76 of the third canister 74 is connected to and extends into the manifold 24. A second end 78 of the third canister 74 is sealed.

The third canister 74, as shown in FIG. 7, is molded such that, by itself, it completely defines the volume $V_3$. As such, the second end 78 of the third canister 74 is sealed. With reference to the embodiment disclosed in FIG. 5, a third cap 80 is inserted into the second end 78 of the third canister 74 and secured with adhesive to seal the second end 78 of the third canister 74. The third cap 80 partially extends into the third canister 74 to decrease the volume $V_3$ of the third canister 74 and to increase contact surface area between the third cap 80 and the third canister 74 for the adhesive.

A third neck 84 is in fluid communication with the duct 30. Furthermore, to minimize the size of the resonating device 10 such that the resonating device 10 is sufficiently compact and can fit into the cabinet 16 with the pump 18, the third neck 84 extends into the third canister 74. More specifically, the third neck 84 includes a proximal end 86 adjacent to the manifold 24 and a distal end 88 opposite the proximal end 86 and defines a third neck duct 90 extending between the ends 86, 88. The distal end 88 of the third neck 84 is suspended in the volume $V_3$ of the third canister 74. That is, the third neck 84 is not in contact with the third canister 74. The third neck 84 is preferably of lesser length and of greater cross-sectional area than the neck 48 and second neck 66, however the length and cross-sectional area of the third neck 84 may vary. The third neck 84 is mounted on the manifold 24 at the proximal end 86 of the third neck 84. The duct 30 is in fluid communication with the third canister 74 through the third neck duct 90. The distal end 88 of the third neck 84 is suspended in the third canister 74, as opposed to connecting the third canister 74 to the distal end 88 of the third neck 84, to maintain structural integrity of the resonating device 10 and to keep the resonating device 10 compact. Preferably, the third neck 84 is cylindrical in shape. However, it is to be appreciated that the third neck 84 can be of any number of shapes, such as the third box-shaped neck 184 of FIG. 8, without deviating from the subject invention.

The third harmonic frequency $F_3$ is triple the first harmonic frequency $F_1$ and is the frequency at which the sound waves are the next loudest to the second harmonic frequency $F_2$. Thus, a greater noise reduction is achieved by attenuating the sound waves at the first harmonic frequency $F_1$, the second harmonic frequency $F_2$, and the third harmonic frequency $F_3$ than by merely attenuating the sound waves at the first harmonic frequency $F_1$ and the second harmonic frequency $F_2$. The third harmonic frequency $F_3$ is defined by the following equation:

$$F_3 = \frac{C}{2\Pi} \sqrt{\frac{A_3}{V_3 L_3}}$$

where $F_3$ is the third harmonic frequency and is a constant with respect to the resonating device 10, C is the velocity of sound at 17° C., $A_3$ is a cross-sectional area of the third neck 84, $V_3$ is the volume of the third canister 74, and $L_3$ is a length of the third neck 84. Preferably, the third harmonic frequency $F_3$ is 300 Hertz or greater. More preferably, the third harmonic frequency $F_3$ is 348 Hertz. The third canister 74 and third neck 84 can be tuned to attenuate sound waves at various frequencies. Additional canisters can be mounted to the resonating device 10 to attenuate sound waves at frequencies other than the first harmonic frequency $F_1$, the second harmonic frequency $F_2$, and the third harmonic frequency $F_3$. However, the most significant noise reduction is experienced by attenuating sound waves at all three harmonic frequencies $F_3$, $F_3$, $F_3$.

A muffler 92 is connected to the outlet 28 and is in fluid communication with the duct 30 for dampening sound waves not attenuated by the canisters 38, 56, 74. Preferably, the muffler 92 extends from the same side of the manifold 24 as the canisters 38, 56, 74 to keep the resonating device 10 compact. However, the muffler 92 can extend from a different side of the manifold 24. The fluid flow exits the resonating device 10 through the muffler 92. Preferably, the muffler 92 is of the type commercially available from Gast Manufacturing, Incorporated. However, the muffler 92 can be any type of muffler capable of fitting with the resonating device 10 inside the cabinet 16.

The inlet 26 includes a first end 94 disposed in the manifold 24 and a second end 96 operatively connected to and extending from the manifold 24. The second end 96 accommodates the flow of fluid from the pneumatic surgical instrument 12. The first end 94 includes a series of annular ribs 98. A tube 100 fits over the first end 94 of the inlet 26 for supplying the flow of fluid to the inlet 26. The annular ribs 98 prevent the tube 100 from slipping off of the first end 94. The first end 94 defines a first cross-sectional area $X_1$ and the second end 96 defines a second cross-sectional area $X_2$. The second cross-sectional area $X_2$ is greater than the first cross-sectional area $X_1$. The increase in cross-sectional area from the first end 94 to the second end 96 helps to smooth the flow of fluid as it flows through the inlet 96, thus dampening the sound waves before the fluid passes over the canisters 38, 56, 74.

Figure 9:
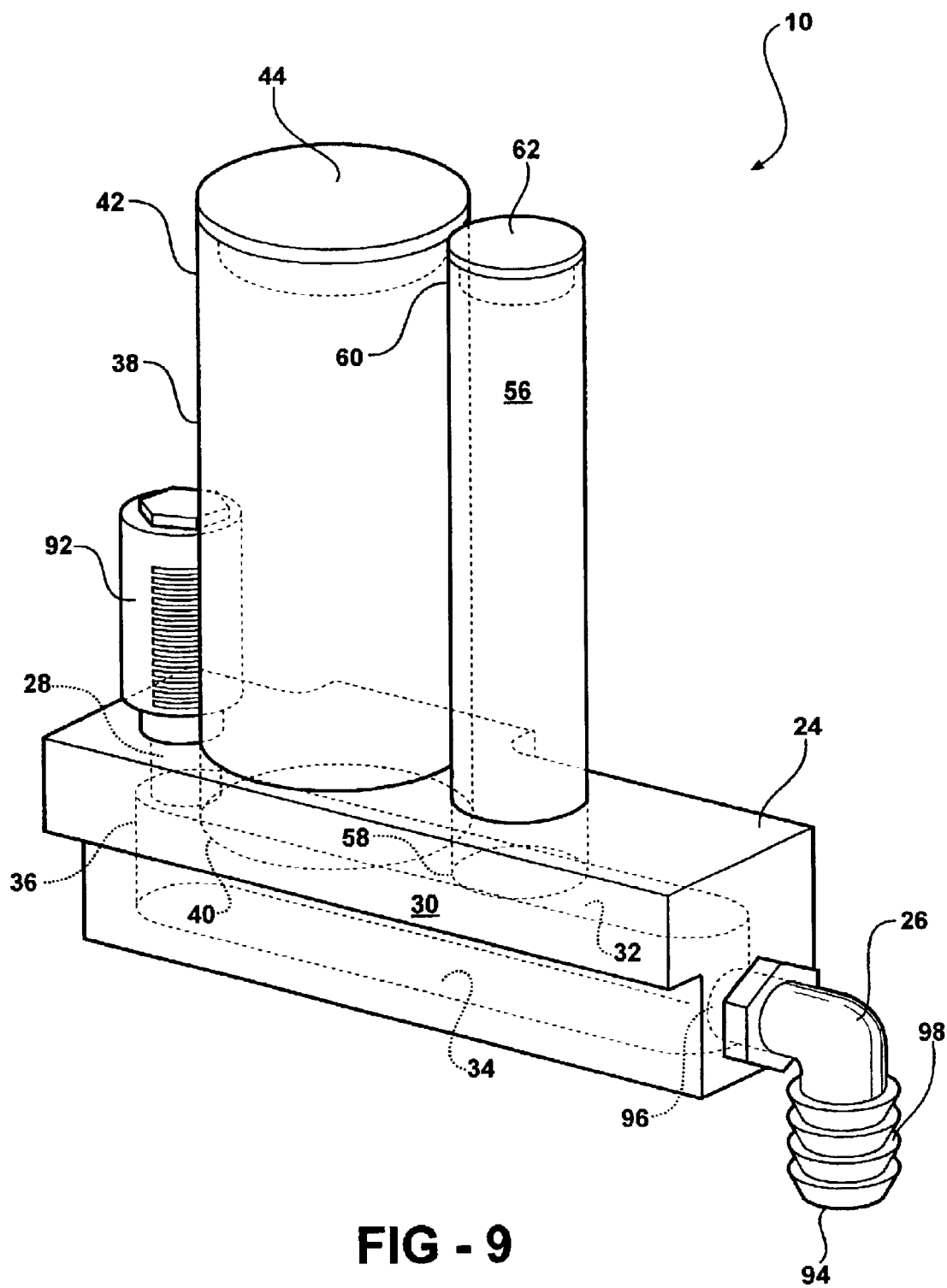
FIG. 9 is a perspective view of another embodiment of the resonating device including the canister and second canister without necks extending into the canisters.

In a further embodiment of the subject invention, shown in FIG. 9, the resonating device 10 is not required to include necks extending into the canisters 38, 56. However, in this embodiment, the arrangement of the canisters 38, 56 is more important. The canisters 38, are arranged to attenuate the highest frequency first, then the next lowest frequency, and so on. The canister 38 and second canister 56 extend from the manifold 24 in series. Preferably, the second canister 56 extends from the manifold 24 independent of the canister 38.

The second canister 56 extends from the manifold 56 closer to the inlet 26 than the canister 38. Thus, the second canister 56 attenuates the sound waves at the second harmonic frequency $F_2$ before the canister 38 attenuates the sound waves at the first harmonic frequency $F_1$. By first attenuating the sound waves at the second harmonic frequency $F_2$, the sound waves at the first harmonic frequency $F_1$ are more efficiently attenuated. The result is greater overall attenuation of the sound waves over alternative canister arrangements.

Figure 10:
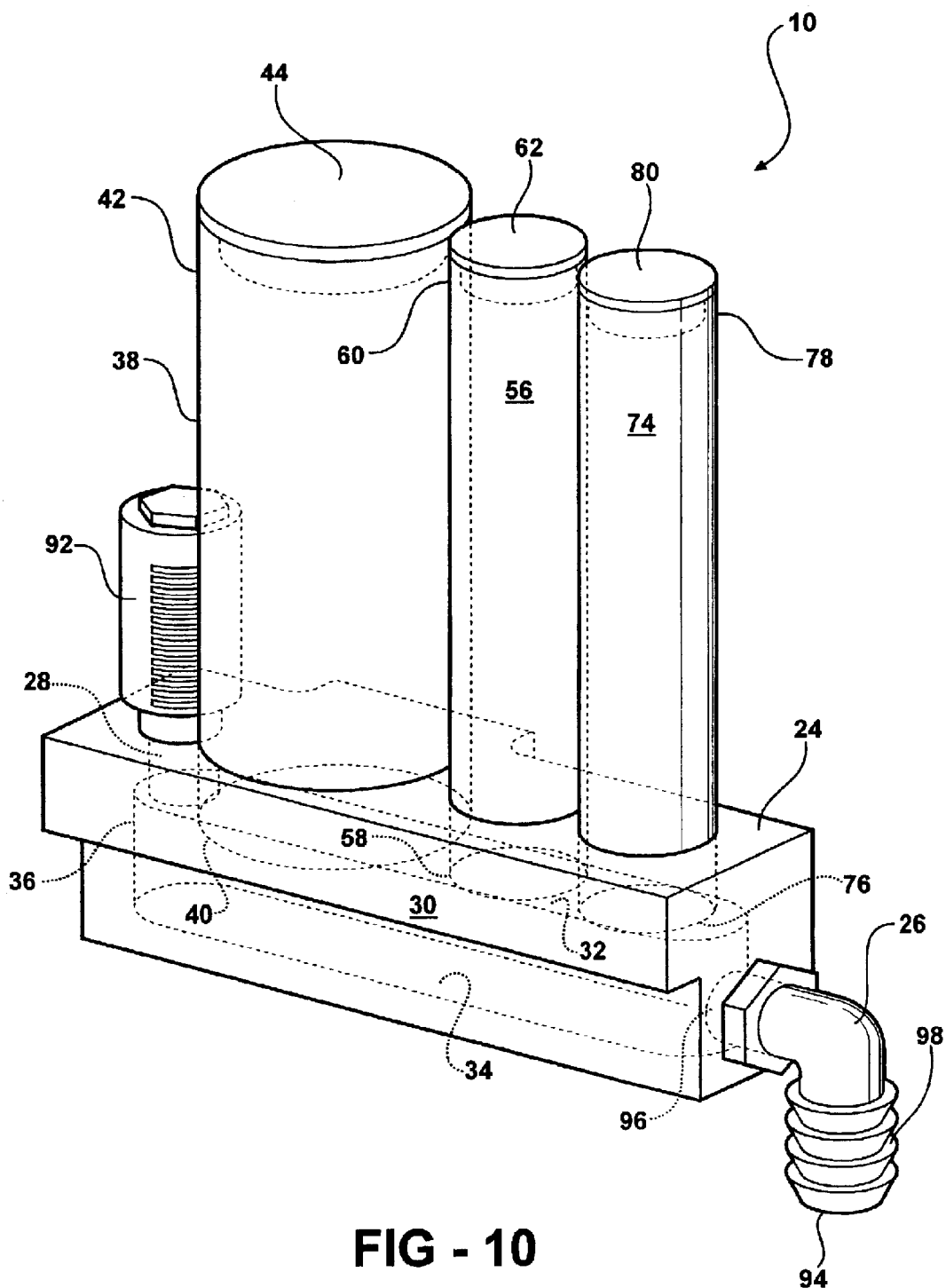
FIG. 10 is a perspective view of the resonating device including the canister, the second canister, and the third canister without necks extending into the canisters.

Preferably, as shown in FIG. 10, the resonating device 10 further includes the third canister 74. Preferably, the third canister 74 extends from the manifold 24 independent of the second canister 56 and the canister 38. The third canister 74 is mounted closer to the inlet 26 than the second canister 56 and the canister 38. Thus, the third canister 74 attenuates the sound waves at the third harmonic frequency $F_3$ before the second canister 56 attenuates the sound waves at the second harmonic frequency $F_2$ and before the first canister 38 attenuates the sound waves at the first harmonic frequency $F_1$. By first attenuating the sound waves at the third harmonic frequency $F_3$, the resonating device 10 even more efficiently attenuates sound waves at the second harmonic frequency $F_2$ and the first harmonic frequency $F_1$ over prior art resonating devices.

Obviously, many modifications and variations of the present invention are possible in light of the above teachings. The invention may be practiced otherwise than as specifically described within the scope of the appended claims. In addition, the reference numerals in the claims are merely for convenience and are not to be read in any way as limiting.

What is claimed is:

1. A resonating device for attenuating sound waves that are generated by a pneumatic surgical instrument (12) during surgery, said device comprising:
    a manifold (24) having an inlet (26) and an outlet (28) and defining a duct (30) extending therebetween for accommodating a flow of fluid from the surgical instrument (12); and
    at least one canister (38) extending from said manifold (24) and defining a volume ($V_1$) for attenuating the sound waves generated by the surgical instrument (12);
    said device characterized by a neck (48) in fluid communication with said duct (30) and extending into said canister (38) to minimize the size of said resonating system (10).

2. A resonating device as set forth in claim 1 wherein said neck (48) includes a proximal end (50) adjacent to said manifold (24) and a distal end (52) opposite said proximal end (50) and being suspended in said volume ($V_1$) of said canister (38).

3. A resonating device as set forth in claim 2 wherein said canister (38) attenuates the sound waves at a first harmonic frequency ($F_1$).

4. A resonating device as set forth in claim 3 wherein said first harmonic frequency ($F_1$) is defined by the following equation:

$$F_1 = \frac{C}{2\Pi} \sqrt{\frac{A_1}{V_1 L_1}}$$

where,
$F_1$ is said first harmonic frequency;
C is a velocity of sound;
$A_1$ is a cross-sectional area of said neck (48);
$V_1$ is said volume of said canister (38); and
$L_1$ is a length of said neck (48).

5. A resonating device as set forth in claim 4 wherein said first harmonic frequency ($F_1$) is 100 Hertz or greater.

6. A resonating device as set forth in claim 4 further comprising a plurality of canisters (55).

7. A resonating device as set forth in claim 6 wherein said plurality of canisters (55) comprises said canister (38) and a second canister (56).

8. A resonating device as set forth in claim 7 wherein said second canister (56) extends from said manifold (24) independent of said canister (38).

9. A resonating device as set forth in claim 8 further comprising a second neck (66) in fluid communication with said duct (30) and extending into said second canister (56).

10. A resonating device as set forth in claim 9 wherein said second neck (66) includes a proximal end (68) adjacent to said manifold (24) and a distal end (70) opposite said proximal end (68) and being suspended in said volume ($V_2$) of said second canister (56).

11. A resonating device as set forth in claim 10 wherein said second canister (56) attenuates the sound waves at a second harmonic frequency ($F_2$).

12. A resonating device as set forth in claim 11 wherein said second harmonic frequency ($F_2$) is defined by the following equation:

$$F_2 = \frac{C}{2\Pi} \sqrt{\frac{A_2}{V_2 L_2}}$$

where,
$F_2$ is said second harmonic frequency;
C is the velocity of sound;
$A_2$ is a cross-sectional area of said second neck (66);
$V_2$ is said volume of said second canister (56); and
$L_2$ is a length of said second neck (66).

13. A resonating device as set forth in claim 12 wherein said second harmonic frequency ($F_2$) is 200 Hertz or greater.

14. A resonating device as set forth in claim 12 wherein said plurality of canisters (55) comprises a third canister (74).

15. A resonating device as set forth in claim 14 wherein said third canister (74) extends from said manifold (24) independent of said second canister (56) and said canister (38).

16. A resonating device as set forth in claim 15 further comprising a third neck (84) in fluid communication with said duct (30) and extending into said third canister (74).

17. A resonating device as set forth in claim 16 wherein said third neck (84) includes a proximal end (86) adjacent to said manifold (24) and a distal end (88) opposite said proximal end (86) and being suspended in said volume ($V_3$) of said third canister (74).

18. A resonating device as set forth in claim 17 wherein said third canister (74) attenuates the sound waves at a third harmonic frequency ($F_3$).

19. A resonating device as set forth in claim 18 wherein said third harmonic frequency ($F_3$) is defined by the following equation:

$$F_3 = \frac{C}{2\Pi}\sqrt{\frac{A_3}{V_3 L_3}}$$

where, $F_3$ is said third harmonic frequency;

C is a velocity of sound;

$A_3$ is a cross-sectional area of said third neck (84);

$V_3$ is said volume of said third canister (74); and $L_3$ is a length of said third neck (84).

20. A resonating device as set forth in claim 19 wherein said third harmonic frequency ($F_3$) is 300 Hertz or greater.

21. A resonating device as set forth in claim 1 further comprising a muffler (92) connected to said outlet (28) and in fluid communication with said duct (30) for dampening sound waves not attenuated by said canister (38).

22. A resonating device as set forth in claim 1 wherein said inlet (26) includes a first end (94) disposed in said manifold (24) and a second end (96) operatively connected to and extending from said manifold (24) for accommodating the flow of fluid from the surgical instrument (12).

23. A resonating device as set forth in claim 22 wherein said first end (94) defines a first inlet cross-sectional area ($X_1$) and said second end (96) defines a second inlet cross-sectional area ($X_2$) with said first inlet cross-sectional ($X_1$) area being greater than said second inlet cross-sectional area ($X_2$).

24. A resonating system for attenuating sound waves, said system comprising:

a pneumatic surgical instrument (12) that generates the sound waves during surgery;

a manifold (24) in fluid communication with said surgical instrument (12) and having an inlet (26) and an outlet (28) and defining a duct (30) extending therebetween for accommodating a flow of fluid from said surgical instrument (12); and at least one canister (38) extending from said manifold (24) and defining a volume ($V_1$) for attenuating sound waves generated by said surgical instrument (12);

said system characterized by a neck (48) in fluid communication with said duct (30) and extending into said canister (38) to minimize the size of said resonating system (14).

25. A system as set forth in claim 21 wherein said neck (48) includes a proximal end (50) adjacent to said manifold (24) and a distal end (52) opposite said proximal end (50) and being suspended in said volume ($V_1$) of said canister (38).

26. A system as set forth in claim 25 wherein said surgical instrument (12) includes a pump (18) for supplying the fluid to said surgical instrument (12).

27. A system as set forth in claim 26 wherein said pump (18) includes a shaft (20) that rotates a plurality of vanes (22) for flowing the fluid from said surgical instrument (12) to said manifold (24).

28. A system as set forth in claim 27 wherein the rotation of said plurality of vanes (22) produces sound waves at a first harmonic frequency ($F_1$), a second harmonic frequency ($F_2$), and a third harmonic frequency ($F_3$).

29. A system as set forth in claim 28 wherein said canister (38) attenuates sound waves at said first harmonic frequency ($F_1$), with said first harmonic frequency ($F_1$) being defined by the following equation:

$$F_1 = R*N$$

where, $F_1$ is said first harmonic frequency;

R is a number of rotations of said shaft (20) per second; and

N is a number of said plurality of vanes (22).

30. A system as set forth in claim 29 wherein said first harmonic frequency ($F_1$) is at least 100 Hertz.

31. A system as set forth in claim 28 wherein said canister (38) attenuates the sound waves at said first harmonic frequency ($F_1$), with said first harmonic frequency ($F_1$) being defined by the following equation:

$$F_1 = \frac{C}{2\Pi}\sqrt{\frac{A_1}{V_1 L_1}}$$

where, $F_1$ is said first harmonic frequency;

C is a velocity of sound;

$A_1$ is a cross-sectional area of said neck (48);

$V_1$ is said volume of said canister (38); and $L_1$ is a length of said neck (48).

32. A system as set forth in claim 31 wherein said first harmonic frequency ($F_1$) is 100 Hertz or greater.

33. A system as set forth in claim 28 further comprising a plurality of canisters (55).

34. A system as set forth in claim 33 wherein said plurality of canisters (55) comprises said canister (38) and a second canister (56).

35. A resonating device as set forth in claim 34 wherein said second canister (56) extends from said manifold (24) independent of said canister (38).

36. A system as set forth in claim 35 further comprising a second neck (66) in fluid communication with said duct (30) and extending into said second canister (56).

37. A system as set forth in claim 36 wherein said second neck (66) includes a proximal end (68) adjacent to said manifold (24) and a distal end (70) opposite said proximal end (68) and being suspended in said volume ($V_2$) of said second canister (56).

38. A system as set forth in claim 37 wherein said second canister (56) attenuates the sound waves at said second harmonic frequency ($F_2$), with said second harmonic frequency ($F_2$) being defined by the following equation:

$$F_2 = 2F_1$$

where, $F_2$ is said second harmonic frequency; and $F_1$ is said first harmonic frequency.

39. A system as set forth in claim 37 wherein said second canister (56) attenuates the sound waves at said second harmonic frequency ($F_2$), with said second harmonic frequency ($F_2$) being defined by the following equation:

$$F_2 = \frac{C}{2\Pi}\sqrt{\frac{A_2}{V_2 L_2}}$$

where, $F_2$ is said second harmonic frequency;

C is the velocity of sound;

$A_2$ is a cross-sectional area of said second neck (66);

$V_2$ is said volume of said second canister (56); and $L_2$ is a length of said second neck (66).

40. A system as set forth in claim 39 wherein said second harmonic frequency ($F_2$) is 200 Hertz or greater.

41. A system as set forth in claim 34 wherein said plurality of canisters (55) further comprises a third canister (74).

42. A resonating device as set forth in claim 41 wherein said third canister (74) extends from said manifold (24) independent of said second canister (56) and said canister (38).

43. A system as set forth in claim 42 further comprising a third neck (84) in fluid communication with said duct (30) and extending into said third canister (74).

44. A system as set forth in claim 43 wherein said third neck (84) includes a proximal end (86) adjacent to said manifold (24) and a distal end (88) opposite said proximal end (86) and being suspended in said volume ($V_3$) of said third canister (74).

45. A system as set forth in claim 44 wherein said third canister (74) attenuates the sound waves at said third harmonic frequency ($F_3$), with said third harmonic frequency ($F_3$) being defined by the following equation:

$$F_3 = 3F_1$$

where, $F_3$ is said third harmonic frequency; and $F_1$ is said first harmonic frequency.

46. A system as set forth in claim 44 wherein said third canister (74) attenuates the sound waves at said third harmonic frequency ($F_3$), with said third harmonic frequency ($F_3$) being defined by the following equation:

$$F_3 = \frac{C}{2\Pi} \sqrt{\frac{A_3}{V_3 L_3}}$$

where, $F_3$ is said third harmonic frequency;

C is the velocity of sound;

$A_3$ is a cross-sectional area of said third neck (84);

$V_3$ is said volume of said third canister (74); and $L_3$ is a length of said third neck (84).

47. A system as set forth in claim 46 wherein said third harmonic frequency ($F_3$) is 300 Hertz or greater.

48. A system as set forth in claim 24 further comprising a cabinet (16) for housing said surgical instrument (12), said manifold (24), said canister (38), and said neck (48).

49. A system as set forth in claim 24 further comprising a muffler (92) connected to said outlet (28) and in fluid communication with said duct (30) for dampening sound waves not attenuated by said canister (38).

50. A resonating device as set forth in claim 24 wherein said inlet (26) includes a first end (94) disposed in said manifold (24) and a second end (96) operatively connected to and extending from said manifold (24) for accommodating the flow of fluid from said surgical instrument (12).

51. A resonating device as set forth in claim 50 wherein said first end (94) defines a first inlet cross-sectional area ($X_1$) and said second end (96) defines a second inlet cross-sectional area ($X_2$) with said first inlet cross-sectional area ($X_1$) being greater than said second inlet cross-sectional area ($X_2$).

52. A resonating device for attenuating sound waves at different harmonic frequencies that are generated by a pneumatic surgical instrument (12) during surgery, said device comprising:

a manifold (24) having an inlet (26) and an outlet (28) and defining a duct (30) extending therebetween for accommodating a flow of fluid from the surgical instrument (12);

a canister (38) and second canister (56) extending from said manifold (24) in series with said canister (38) defining a volume ($V_1$) for attenuating the sound waves that are generated by the surgical instrument (12) at a first harmonic frequency ($F_1$) and with said second canister (56) defining a volume ($V_2$) for attenuating the sound waves that are generated by the surgical instrument (12) at a second harmonic frequency ($F_2$) wherein said first harmonic frequency ($F_1$) is a lowest harmonic frequency and said second harmonic frequency ($F_2$) is greater than said first harmonic frequency ($F_1$);

said device characterized by said second canister (56) extending from said manifold (24) closer to said inlet (26) than said canister (38) such that the sound waves that are generated at said second harmonic frequency ($F_2$) are attenuated by said second canister (56) before the sound waves that are generated at said first harmonic frequency ($F_1$) are attenuated by said canister (38) upon flow of the fluid into said manifold (24) through said inlet (26).

53. A resonating device as set forth in claim 52 wherein said second canister (56) extends from said manifold (24) independent of said canister (38).

54. A resonating device as set forth in claim 53 further comprising a neck (48) in fluid communication with said duct (30) and said canister (38) and a second neck (66) in fluid communication with said duct (30) and said second canister (56).

55. A resonating device as set forth in claim 54 wherein said first harmonic frequency ($F_1$) is defined by the following equation:

$$F_1 = \frac{C}{2\Pi} \sqrt{\frac{A_1}{V_1 L_1}}$$

where, $F_1$ is said first harmonic frequency;

C is a velocity of sound;

$A_1$ is a cross-sectional area of said neck (48);

$V_1$ is said volume of said canister (38); and $L_1$ is a length of said neck (48).

56. A resonating device as set forth in claim 55 wherein said first harmonic frequency ($F_1$) is 100 Hertz or greater.

57. A resonating device as set forth in claim 55 wherein said second harmonic frequency ($F_2$) is defined by the following equation:

$$F_2 = \frac{C}{2\Pi} \sqrt{\frac{A_2}{V_2 L_2}}$$

where, $F_2$ is said second harmonic frequency;

C is a velocity of sound;

$A_2$ is a cross-sectional area of said second neck (66);

$V_2$ is said volume of said second canister (56); and $L_2$ is a length of said second neck (66).

58. A resonating device as set forth in claim 57 wherein said second harmonic frequency ($F_2$) is 200 Hertz or greater.

59. A resonating device as set forth in claim 57 wherein said plurality of canisters (55) further comprises a third canister (74) extending from said manifold (24) in series with said canister (38) and said second canister (56) closer to said inlet (26) than said second canister (56) and defining a third volume ($V_3$) for attenuating the sound waves that are generated by the surgical instrument (12) at a higher harmonic frequency than the sound waves attenuated by said second canister (56) wherein said higher harmonic frequency is a third harmonic frequency ($F_3$).

60. A resonating device as set forth in claim 59 wherein said third canister (74) extends from said manifold (24) independent of said second canister (56) and said canister (38).

61. A resonating device as set forth in claim 60 wherein said third harmonic frequency ($F_3$) is defined by the following equation:

$$F_3 = \frac{C}{2\Pi}\sqrt{\frac{A_3}{V_3 L_3}}$$

where, $F_3$ is said third harmonic frequency;

C is a velocity of sound;

$A_3$ is a cross-sectional area of said third neck (84);

$V_3$ is said volume of said third canister (74); and $L_3$ is a length of said third neck (84).

62. A resonating device as set forth in claim 61 wherein said third harmonic frequency ($F_3$) is 300 Hertz or greater.

63. A resonating device as set forth in claim 52 wherein said necks extend into said canisters.

64. A resonating device as set forth in claim 52 further comprising a muffler (92) connected to said outlet (28) and in fluid communication with said duct (30) for dampening sound waves not attenuated by said canister (38) and said second canister (56).

65. A resonating device as set forth in claim 52 wherein said inlet (26) includes a first end (94) disposed in said manifold (24) and a second end (96) operatively connected to and extending from said manifold (24) for accommodating the flow of fluid from said surgical instrument (12).

66. A resonating device as set forth in claim 65 wherein said first end (94) defines a first inlet cross-sectional area ($X_1$) and said second end (96) defines a second inlet cross-sectional area ($X_2$) with said first inlet cross-sectional area ($X_1$) being greater than said second inlet cross-sectional area ($X_2$).

* * * * *